US008263119B2

(12) United States Patent
Withington

(10) Patent No.: US 8,263,119 B2
(45) Date of Patent: Sep. 11, 2012

(54) CAPSULE FORMULATIONS CONTAINING LANTHANUM COMPOUNDS

(75) Inventor: Roger Withington, Surrey (GB)

(73) Assignee: Shire LLC, Florence, KY (US)

( * ) Notice: Subject to any disclaimer, the term of this patent is extended or adjusted under 35 U.S.C. 154(b) by 0 days.

(21) Appl. No.: 12/958,380

(22) Filed: Dec. 1, 2010

(65) Prior Publication Data
US 2012/0141580 A1 Jun. 7, 2012

(51) Int. Cl.
A61K 9/20 (2006.01)
A61K 31/28 (2006.01)
A61K 33/00 (2006.01)
A01N 59/00 (2006.01)
A01N 55/02 (2006.01)

(52) U.S. Cl. ......... 424/452; 424/715; 514/492; 514/962
(58) Field of Classification Search ........................ None
See application file for complete search history.

(56) References Cited

U.S. PATENT DOCUMENTS

| 4,428,927 | A * | 1/1984 | Ebert et al. ..................... 424/440 |
| 5,030,447 | A * | 7/1991 | Joshi et al. ..................... 514/510 |
| 5,968,976 | A | 10/1999 | Murrer et al. |
| 7,381,428 | B2 | 6/2008 | Ferdinando et al. |
| 7,465,465 | B2 | 12/2008 | Haslam et al. |
| 7,618,656 | B2 | 11/2009 | Hallenbeck et al. |
| 2006/0121127 | A1 * | 6/2006 | Ferdinando et al. .......... 424/617 |
| 2006/0153932 | A1 | 7/2006 | Ferdinando et al. |
| 2007/0259052 | A1 | 11/2007 | Hallenbeck et al. |
| 2008/0187602 | A1 | 8/2008 | Ferdinando et al. |
| 2009/0017133 | A1 | 1/2009 | Haslam et al. |

FOREIGN PATENT DOCUMENTS

| EP | 1785141 A1 | 5/2007 |
| WO | 2010-085520 A1 | 7/2010 |
| WO | 2010-106557 A2 | 9/2010 |

OTHER PUBLICATIONS

Capsugel, Coni-Snap Capsules, Reliable and Consistent Two-Piece Capsules, brochure, Feb. 2008.
Stegemann and Bornem, Hard Gelatin Capsules Today- and Tomorrow,Capsugel Library, 2nd Edition, 2002.
Tousey, The Granulation Process 101: Basic Technologies for Tablet Making, Pharmaceutical Technology: Tableting & Granulation 2002, pp. 8-13.
International Search Report and Written Opinion for International Patent Application No. PCT/US2011/062716 mailed Feb. 1, 2012.

* cited by examiner

Primary Examiner — Ernst Arnold
(74) Attorney, Agent, or Firm — Frommer Lawrence & Haug LLP; Shelly M. Fujikawa

(57) ABSTRACT

The present invention includes an oral pharmaceutical capsule comprising a shell, lanthanum carbonate or lanthanum carbonate hydrate, and a lubricant such as talc, wherein the shell encapsulates the lanthanum carbonate or lanthanum hydrate and the lubricant. Capsule shells comprise, for example, gelatin. The capsules of the present invention dissolve at a similar rate before and after storage. The oral pharmaceutical capsules of the present invention can be administered to treat a patient at risk for or suffering from hyperphosphatemia, at risk for or suffering from chronic kidney disease (CKD), at risk for or suffering from soft tissue calcification associated with CKD, or at risk for or suffering from secondary hyperparathyroidism.

16 Claims, 9 Drawing Sheets

CAPSULE FORMULATIONS CONTAINING LANTHANUM COMPOUNDS

FIELD OF THE INVENTION

The present invention includes an oral pharmaceutical capsule comprising a gelatin shell that encapsulates both lanthanum carbonate or lanthanum carbonate hydrate and a lubricant such as talc. The capsules of the present invention dissolve at a similar rate before and after storage. The oral pharmaceutical capsules of the present invention can be administered to treat a patient at risk for or suffering from hyperphosphatemia, at risk for or suffering from chronic kidney disease (CKD), at risk for or suffering from soft tissue calcification associated with CKD, or at risk for or suffering from secondary hyperparathyroidism.

BACKGROUND OF THE INVENTION

Hyperphosphatemia is a particular problem of patients with chronic renal insufficiency or chronic kidney disease (CKD). Approximately 70% of patients with end stage renal disease (ESRD) on renal dialysis therapy require treatment for hyperphosphatemia. This condition can lead to severe bone problems and metastatic calcification of skin and major organs and is associated with significant morbidity and mortality. Conventional dialysis fails to reduce the levels of phosphate in the blood, so that levels rise in time. Elevated phosphate levels are treated using a combination of dietary restrictions and phosphate-binding agents. Chronic renal insufficiency patients also suffer from secondary hyperparathyroidism.

Certain forms of lanthanum carbonate have been used to treat hyperphosphatemia in patients with renal failure (see, e.g., JP 1876384). U.S. Pat. No. 5,968,976, owned by the assignee of the present invention, describes the preparation and use in a pharmaceutical composition of certain hydrates of lanthanum carbonate for the treatment of hyperphosphatemia. U.S. Pat. Nos. 7,381,428 and 7,465,465, also both owned by the assignee of the present invention, disclose formulations containing lanthanum carbonate and lanthanum carbonate hydrate.

The non-calcium, non-resin phosphate binder lanthanum carbonate as a chewable tablet (FOSRENOL®, Shire Pharmaceuticals, Basingstoke, UK) is commonly used in clinical practice for the reduction of serum phosphorus in patients with CKD Stage 5 who are undergoing dialysis. For patients who have trouble chewing lanthanum carbonate tablets, who find chewable tablets unpalatable, or who find chewing tablets several times per day tiresome, there is a need in the art for alternative formulations containing lanthanum carbonate or lanthanum carbonate hydrate.

SUMMARY OF THE INVENTION

The present invention includes an oral pharmaceutical capsule comprising a shell that encapsulates both lanthanum carbonate or lanthanum carbonate hydrate and a lubricant such as talc. The shell of the capsule includes, for example, gelatin. The capsules of the present invention dissolve at a similar rate before and after storage. Capsules can include additional encapsulated excipients such as diluents, disintegrants, and flow aids.

The oral pharmaceutical capsules of the present invention can be administered to treat a patient at risk for or suffering from hyperphosphatemia. Further uses of the pharmaceutical capsules include treating a patient (1) at risk for or suffering from chronic kidney disease (CKD), (2) at risk for or suffering from soft tissue calcification associated with chronic kidney disease (CKD), or (3) at risk for or suffering from secondary hyperparathyroidism by administering the capsules of the invention to the patient.

DETAILED DESCRIPTION OF THE INVENTION

Figure 1:
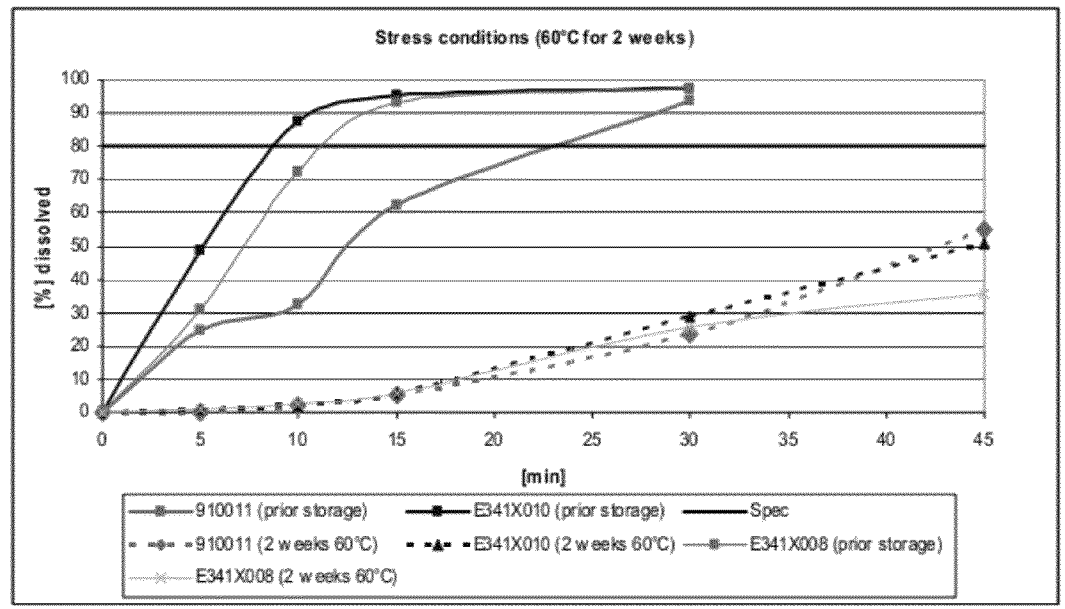
FIG. 1 is a graph comparing the dissolution rates of 3 lanthanum carbonate capsules (E341x008, E341X010, and 910011) before and after storage for 2 weeks at 60° C.

Capsule formulations provide a palatable alternative to chewable tablets. Like chewable tablets, capsules can be administered without liquid which is advantageous for patients with kidney disease who must regulate their liquid intake. Capsules can be chewed like a tablet or, for patients who have difficulty chewing, capsules can be opened and the contents can be sprinkled onto the tongue or onto food. Alternatively, capsules can be swallowed whole.

The present invention is based on the unexpected finding that the dissolution rate of oral pharmaceutical capsules where the shell encapsulates both lanthanum carbonate hydrate and talc are unaffected by storage while other encapsulated lubricants cause a reduction in the dissolution rate of capsules as demonstrated in the Examples. A consistent dissolution rate before and after storage is necessary for regulatory approval, provides a consistent rate and extent of phosphate binding, and allows for greater shelf-life.

The terms "about" or "approximately" mean within an acceptable range for the particular parameter specified as determined by one of ordinary skill in the art, which will depend in part on how the value is measured or determined, e.g., the limitations of the measurement system. For example, "about" can mean a range of up to 20% of a given value. Alternatively, particularly with respect to biological systems or processes, the term can mean within an order of magnitude, preferably within 5-fold, and more preferably within 2-fold, of a value.

Oral Pharmaceutical Capsules

Oral pharmaceutical capsules include a shell that encapsulates an active ingredient such as lanthanum carbonate or lanthanum carbonate hydrate, and other optional ingredients such as a lubricant. The encapsulated material can be a powder.

A capsule shell can be a hard gel. Hard gel capsule shells typically have a body and a cap. The body and cap materials can comprise a gelling agent and water. The gelling agent can be, but is not limited to, gelatin, modified starch, carrageenan, gellan, mannan gum, amylose, xanthan, alginates, agar, guar, gum arabic, pectin, cyclodextrin or a combination thereof. The shell can optionally include a gelling salt, a plasticizer, an emulsifier, thickener, preservative, flavoring, sweetener, pigment, radiation blocker, opacifying agent, anti-oxidant, masticatory substance, etc.

Gelatin can be manufactured by the partial hydrolysis of collagen from animal by-products such as bones, skin, and connective tissue. Bovine and porcine animals are the primary sources of gelatin.

Modified starches, include, for example, non-retrograding starches derived by chemical modification of starch from any plant source such as corn, waxy maize, potato, wheat, rice, tapioca, sorghum, etc. Useful modified starches are ether and ester derivatives of starch including, for example, hydroxypropyl, hydroxyethyl, succinate, and octenyl succinate starch derivatives. Other modified starches which may be used include the thermally converted, fluidity or thin boiling type products derived from the above chemically modified starches. These materials may be of lower molecular weight, prepared by heating the modified starch, subjecting the starch to hydrolytic acid and/or heat treatment, etc.

Carrageenan is a natural sulfated polysaccharide hydrocolloid derived from seaweed, and is a mixture of galactose and 3-6-anhydrogalactose copolymers. A number of different carrageenan types exist (e.g., kappa, iota, lambda, etc.) and it is anticipated that any of these may be used in the present invention.

Gellan gum is an extracellular polysaccharide obtained by aerobic fermentation of the microorganism, *Pseudomonas elodea*. Various forms of gellum gum including, but not limited to, native, deacetylated, deacylated clarified, partially deacetylated, partially deacylated clarified may be used in the present invention.

Mannam gum includes the galactomannan gums, the glucomannan gums and mixtures thereof. Accordingly, mannam gum includes, but is not limited to, locust bean gum, konjac gum, tara gum and cassia gum.

A gelling salt may be used in the present invention. Accordingly, a calcium salt, a magnesium salt, a barium salt, a sodium salt or a potassium salt of an appropriate inorganic or organic acid may be used to form the shell of a capsule of the present invention.

Plasticizers can also be added to the shell of a capsule formulation. Plasticizers can be polyols, for example, glycerin, sorbitol, an alkylene glycol, maltitol, lactitol, xylitol, corn syrup solids, etc. or a combination thereof.

Pigments can include indigotine (i.e., FD & C Blue 2), erythrosin (i.e., FD & C Red 3), and titanium dioxide, which also acts as an opacifier.

The body and cap of the capsule shell can comprise between about 10 wt % and 95 wt % gelling agent (e.g., gelatin), between about 75 wt % to about 95 wt % gelling agent, or between about 80 wt % and 90 wt % gelling agent of the weight of the shell. The body and cap of the capsule shell can comprise between about 5 wt % and 40 wt % water, between about 5 wt % and about 25 wt % water, or between about 10 wt % and 20 wt % water based on the total weight of the shell. The body and cap of the capsule shell can comprise up to about 10 wt % pigment, between about 0.1 wt % and about 2.5 wt % pigment, or between about 1.5 wt % and 2.5 wt % pigment of the weight of the shell.

Capsule shells can be purchased for example from Capsugel® (Peapack, N.J.) and Shionogi Qualicaps® (Whitsett, N.C.). Shells that can be used to encapsulate lanthanum carbonate formulations can be, for example, Capsugel® ConiSnap® size 00 for 500 mg capsules and Capsugel® ConiSnap® 0el (0 elongated) for 375 mg capsules, where the masses are based on the mass of elemental lanthanum in the lanthanum carbonate. The capsule can be tubular in shape and from about 0.4 inches to about 1.1 inches in closed length and from about 0.18 to about 0.4 inches in diameter with a volume of about 0.1 to about 1.4 mL. Briefly, capsule shells are made by dipping rods having dimensions of the cap and body of the capsule into a melted, pigmented gelatin solution, allowing the cap and body to solidify while rotating the rods to distribute the gelatin evenly, removing the cap and body from the rods, and fitting the cap and body with each other.

Several methods of producing capsules containing a powder are known in the art. The method generally includes optionally sieving the encapsulated ingredients of the capsule, mixing the ingredients, optionally slugging or roller compacting followed by milling to produce a coarse powder, and optionally sieving the coarse powder. The powder is then placed into one half of the capsule and the other half of the capsule shell is pressed onto the first half. See Stegemann and Bornem, "Hard gelatin capsules today—and tomorrow," $2^{nd}$ Edition 2002 from the Capsugel® Library and Tousey, "The Granulation Process 101: Basic Technologies for Tablet Making," *Pharmaceutical Technology: Tableting & Granulation* 2002, pages 8-13.

A capsule can be tested for its stability during storage by storing the capsule under accelerated aging conditions and testing the capsule for its ability to dissolve before and after storage. Accelerated aging conditions include 25° C., 30° C., 40° C., 50° C., 60° C., 70° C., or 80° C. for 1, 2, 3, or 4 weeks or a month optionally at 55%, 60%, 65%, 70%, 75%, or 80% relative humidity (RH). These conditions can be correlated with room temperature conditions using the Arrhenius equation which relates rate of reaction (in this case, degradation/instability) to temperature. Conditions can also be internationally recognized standard conditions such as 25° C./60% RH, 25° C./65% RH, 30° C./60% RH, 30° C./65% RH, 30° C./75% RH, or 40° C./75% RH, 45° C./75% RH for 1, 2, 3, or 4 weeks or a month. Capsules before and after storage can be compared by testing their ability to dissolve in solution over time. For example as discussed in the Examples, capsules can be exposed to a 0.25 M HCl solution and the amount of dissolved lanthanum carbonate or lanthanum carbonate hydrate can be measured over time by titrating the lanthanum in solution with EDTA. The capsules of the present invention can be at least 60%, 70%, 80%, 90%, or 100% dissolved (based on, e.g., the amount of dissolved lanthanum) after 10, 20, 30, 45, or 60 minutes in a solution (e.g., 0.25 M HCl) after the capsules have been exposed to accelerated aging conditions. For example, the capsules of the present invention can be at least 80% dissolved (based on the amount of dissolved lanthanum) after 30 minutes in 0.25 M HCl after storage at 50° C. or 60° C. for 1 or 2 weeks.

Lanthanum Carbonate and Lanthanum Carbonate Hydrate

"Lanthanum carbonate" as used herein encompasses all hydrated forms of lanthanum carbonate as well as anhydrous lanthanum carbonate.

The capsule formulations of the invention can contain lanthanum carbonate having the general formula $La_2(CO_3)_{0.3} \cdot xH_2O$, wherein x has a value from 0 to 10. Preferably, x has a value from 3 to 8, desirably from 3 to 6. Most preferably, x may have an average value of about between 4 and 5. The hydration level of the lanthanum compound can be measured by methods well known in the art, such as x-ray powder diffraction (XRPD).

The amount of lanthanum carbonate encapsulated in the shell of the capsule ranges from about 50 wt % to about 95 wt %, preferably from about 75 wt % to about 90 wt %, and most preferably from about 85 wt % to about 90 wt % based on the total weight of the contents of the capsule. In one embodiment, the amount of lanthanum carbonate encapsulated in the shell of the capsule is about 87 wt % based on the total weight of the contents of the capsule.

The amount of elemental lanthanum as lanthanum carbonate encapsulated in the shell of the capsule ranges from about 26 wt % to about 50 wt %, preferably from about 35 wt % to about 50 wt % and most preferably from about 40 wt % to about 50 wt % based on the total weight of the contents of the capsule. In one embodiment, the amount of elemental lanthanum as lanthanum carbonate encapsulated in the shell of the capsule is about 45 wt % based on the total weight of the contents of the capsule.

The amount of elemental lanthanum in the lanthanum carbonate capsule can be 250 mg, 350 mg, 500 mg, 750 mg, or 1000 mg and preferable 250 mg, 350 mg, or 500 mg.

Additional Encapsulated Ingredients

Additional ingredients that can be encapsulated by the shell include diluents, lubricants, flow aids, binders, disintegrants, colors, flavors, antioxidant, and sweeteners. The additional encapsulated ingredients should be suitable for oral administration to renally impaired subjects.

A diluent can be added to the tablet formulation in an amount from about 5 wt % to about 50 wt % based on the total weight of the capsule contents of the capsule. The total diluent amount can be from about 5 wt % to about 30 wt %, preferably from about 5 wt % to about 20 wt %, and most desirably from about 5 wt % to about 10 wt % based on the total weight of the capsule contents of the formulation.

Diluents include a monosaccharide, a disaccharide, calcium sulfate dihydrate, an oligosaccharide, isomaltooligosaccharide, erythritol, polydextrose, dextrins, starch, maltodextrin, calcium lactate trihydrate, microcrystalline cellulose (such as Avicel™ available from GFS Chemicals (Powell, Ohio)), hydrolyzed cereal solids (such as Maltrons or Mor-Rex™), amylose, or glycine. One or more diluents can be present in the formulation.

Suitable monosaccharides for use in the formulation of the present invention include, but are not limited to, glyceraldehyde, erythrose, threose, ribose, lyxose, xylose, arabinose, allose, talsoe, gulose, mannose, glucose (e.g., in the form of corn syrup), idose, galactose, altrose, dihydroxyacetone, erythrulose, ribulose, xyloketose, psicose, tagatose, sorbose, fructose, sorbitol, xylitol, inositol, erythritol, and mannitol in either the D- or L-configuration, including derivatives and analogs thereof. Monosaccharides for use in this invention can be either cyclic (in either alph- or beta-form) or acyclic and can be used in the invention as mixtures. Other suitable monosaccharides include dextrose (D-glucose such as Cerelose™ available from Fisher Scientific (Hampton, N.H.)).

Suitable disaccharides for use in the present invention include, but are not limited to, sucrose (for example, in the form of Di-Pac™ available from Domino Foods in Baltimore, Md., Sugartab™ available from JRS Pharma (Patterson, N.Y.), confectioner's sugar, or Nutab), lactose (including anhydrous lactose and lactose monohydrate), maltose, isomaltose, cellobiose, trehalose, maltitol (in the form of Lycasin™ available from Roquette (Lestrem, France)), isomalt, lactitol, mixtures, derivatives, and analogs thereof. Disaccharides of this invention also include any combination of two monosaccharides linked by a glycosidic bond. Disaccharides can be either homodisaccharides (i.e., consisting of 2 monosaccharides that are the same) or heterodisaccharides (i.e., consisting of 2 monosaccharides that are different). Furthermore, monosaccharides and disaccharides can be used in the same formulation.

Other suitable monosaccharides and disaccharides can be found in Remington: The Science and Practice of Pharmacy ($20^{th}$ Edition, A. R. Gennaro editor, Lippincott Baltimore, Md.: Williams and Wilkins, 2000) at pages 409-413; and in Biochemistry ($2^{nd}$ Edition, Voet and Voet, New York: John Wiley & Sons, Inc., 1995) at pages 251-276. Hydrolyzed starches containing mono- and/or disaccharides can also be used in the formulations of the invention.

Dextrates can also be used as a monosaccharide/disaccharide diluent. The term "dextrates" as used herein refers to a purified mixture of saccharides that is mostly dextrose (e.g., not less than about 93.0% and not more than about 99.0%, calculated on the dried basis) and that results from a controlled enzymatic hydrolysis of starch. Dextrates can be either anhydrous or hydrated. "Dextrates" can refer to dextrates as defined in the official monograph found in National Formulary 21 (printed by Webcom Limited in Toronto, Canada; 2003). Dextrates are available from JRS Pharma (Patterson, N.Y.) as Emdex™.

Useful lubricants can be chosen from, for example, magnesium stearate, talc, mineral oil (liquid paraffin), polyethylene glycol, silica, colloidal anhydrous silica, colloidal silicon dioxide, hydrogenated vegetable oil, glyceryl behenate, L-leucine, L-leucine/polyethylene glycol 6000, polyethylene glycol 6000 or glyceryl monostearate. Useful flow aids can be chosen from, for example, silica, colloidal anhydrous silica, or colloidal silicon dioxide. Generally, lubricants stop a formulation from sticking to the process equipment while flow aids enable the formulation to flow freely while being processed. One ingredient can be both a lubricant and a flow aid. One or more lubricants can be present in a formulation. One or more flow aids can be present in a formulation. In one embodiment, the lubricant can be talc and the flow aid can be colloidal silicon dioxide.

The lubricant amount can be from about 0.01% to about 0.05%, preferably from about 0.01% to about 0.04%, and most desirably from about 0.01% to about 0.03% by weight of the capsule contents of the formulation. The flow aid amount can be from about 0.1% to about 4%, preferably from about 0.1% to about 3%, and most desirably from about 0.1% to about 2% by weight of the capsule contents of the formulation.

Disintegrants can be chosen from crospovidone, croscarmellose sodium, starches such as sodium starch glycolate and pregelatinized corn starches, clays, celluloses such as purified cellulose, microcrystalline cellulose, methylcellulose, carboxymethylcellulose and sodium carboxymethylcellulose, alginates, and gums such as agar, guar, locust bean, karaya, pectin and tragacanth gums. One or more disintegrants can be present in a formulation. The total disintegrant amount can be from about 1.0 wt % to about 15 wt %, preferably from about 3 wt % to about 10 wt %, and most desirably from about 3 wt % to about 5 wt % by weight of the capsule contents of the formulation.

Combination Therapies

Lanthanum carbonate capsules can be administered with vitamin D, a calcium source, vitamin K, or a combination thereof. These additional ingredients can be encapsulated with the lanthanum carbonate or administered separately.

Often, a subject suffering from hyperphosphatemia or the symptoms of CKD is vitamin D deficient. Levels of 25-hydroxy vitamin $D_2$ are low at values less than about 16 ng/mL and replacement treatment aims for levels of greater than or equal to about 16 ng/mL. Levels of 1,25-dihydroxy vitamin $D_2$ are low at values less than about 22 pg/mL and replacement treatment aims for levels of greater than about 22 pg/mL. Thus, it becomes desirable to produce and administer to a patient a formulation containing lanthanum carbonate and vitamin D or an analog of vitamin D or to administer to a patient a separate formulation containing lanthanum carbonate and a separate formulation containing vitamin D or an analog of vitamin D.

Examples of vitamin D sources which may be used include 1,25 dihydroxy-vitamin D, the active metabolite of vitamin D (calcitriol, rocalcitrol). Examples of suitable vitamin D analogs include doxercalciferol (Hectorol™, available from Bone Care International, Middleton, Wis.) and paricalcitol (Zemplar™, available from Abbott Laboratories, Abbott Park, Ill.). One or more vitamin D sources or vitamin D analogs can be present in a formulation.

When Vitamin D is administered in a separate dosage form, 100 USP units of vitamin D can be administered once per day to a patient requiring treatment.

Hyperphosphatemic subjects or subjects having symptoms of CKD often suffer from hypocalcaemia (i.e., a blood calcium concentration below about 8.5 mg/dL). Hence, a formulation of the invention can include lanthanum carbonate and a calcium source.

Examples of forms of calcium include calcium carbonate (e.g., Tums™ available from GlaxoSmithKline, Uxbridge, UK), calcium acetate (e.g., PhosLo™ available from Nabi Biopharmaceuticals, Boca Raton, Fla.), and $CaCl_2$. One or more calcium sources can be present in a formulation.

A calcium source can also be administered in a separate dosage form, but concurrently with the dosage form of this invention. In a specific embodiment, 1-2 tablets containing 200 mg as calcium are given 3 times per day to a patient requiring treatment.

A subject suffering from hyperphosphatemia or the symptoms of CKD can be vitamin K deficient. In another embodiment of the present invention, the formulation of the invention, in combination with vitamin K, is administered to a subject suffering from hyperphosphatemia or the symptoms of CKD to alleviate vitamin K deficiency. Examples of vitamin K sources include vitamin K1 (phylloquinone), vitamin K2 (menaquinone), and vitamin K3 (menadione).

Vitamin K can be combined in the same formulation as the lanthanum formulation or can be given in a different formulation. In a specific embodiment, 2.5 to 25 mg of vitamin K1 are administered once per day to a subject requiring treatment.

Treatment Methods

Subjects susceptible to or suffering from hyperphosphatemia, at risk for chronic kidney disease (CKD), having stage one to five CKD, susceptible to or suffering from soft tissue calcification associated with CKD, susceptible to or suffering from secondary hyperparathyroidism, or susceptible to or suffering from other as yet undiscovered conditions requiring control of phosphate absorption, can be treated by administering a therapeutically effective amount of a lanthanum carbonate capsule formulation of the present invention.

As used herein, the terms "treat," "treating," or "treatment" mean the prevention, reduction, amelioration, partial or complete alleviation, or cure of hyperphosphatemia, chronic kidney disease (CKD), severe bone problems, soft tissue calcification, secondary hyperparathyroidism, or other as yet undiscovered conditions requiring control of phosphate absorption.

Further, as used herein, the term "subject" refers to a mammal (e.g., any veterinary medicine patient such as a domesticated animal, such as a dog or cat), or a human patient.

A "pharmaceutically effective amount" or "therapeutically effective amount" as used herein is an amount or dose of lanthanum carbonate sufficient (i) to detectably decrease the serum phosphate levels of a subject or (ii) at a minimum, to keep the serum phosphate levels of a subject substantially constant.

The term "symptom(s)" of those at risk for or having hyperphosphatemia, CKD, soft tissue calcification associated with CKD, or secondary hyperparathyroidism may be any functional or structural abnormality experienced by a subject and indicating kidney dysfunction. Among other abnormalities, as an example, one or more of the following symptoms may indicate risk for or the presence of CKD: a creatinine concentration of above about 1.6 mg/dL, a blood urea nitrogen (BUN) of above about 20 mg/dL, a blood phosphate level of above about 4.5 mg/dL, any detectable amount of blood in the urine, a urine protein concentration above about 100 mg/dL, a urine albumin concentration above about 100 mg/dL, an intact parathyroid hormone (PTH) concentration in the blood of above about 150 pg/mL, or a glomerular filtration rate (GFR) of below about 90 mL/min/1.73 $m^2$.

Subjects susceptible to or suffering from hyperphosphatemia can be treated by administering a therapeutically effective amount of a lanthanum carbonate formulation of the invention. Hyperphosphatemia as used herein refers to a condition of a patient having blood phosphate levels of above about 4.5 mg/dL.

The National Kidney Foundation-Kidney Disease Outcomes Quality Initiative ("NKF-K/DOQI" or "K/DOQI," as referred to herein) has defined chronic kidney disease (CKD) as either (1) having kidney damage as defined by structural or functional abnormalities of the kidney for 3 months or longer with or without a decreased glomerular filtration rate (GFR) or (2) having a GFR of less than 60 mL/min/1.73 $m^2$ for 3 months or longer with or without kidney damage. Structural or functional abnormalities are manifested by symptoms such as either pathologic abnormalities or markers of kidney damage, including abnormalities identified in imaging studies or the composition of blood or urine.

Examples of markers of kidney damage include a plasma creatinine concentration of above about 1.6 mg/dL and a blood urea nitrogen (BUN) concentration of above about 20 mg/dL. Typically, both of these markers are elevated in individuals with CKD. Additional markers of kidney damage can include hematuria (i.e., any detectable amount of blood in the urine), proteinuria (i.e., protein concentrations in urine above about 100 mg/dL), albuminuria (i.e., albumin concentrations in urine above about 100 mg/dL), an intact parathyroid hormone (PTH) concentration in the blood above about 150 pg/mL, or blood phosphate levels of above about 4.5 mg/dL. One specific marker of kidney disease is a GFR rate above normal (i.e., a GFR above about 90 mL/min/1.73 m$^2$), however a below normal GFR also indicates CKD.

K/DOQI has published guidelines that define five different stages of CKD (Am J Kidney Dis. 2001, 37(suppl 1):S1-5238). The following table provides a description of each of the five stages of CKD and the GFR ranges for each of the stages.

TABLE 1

Five Stages of Chronic Kidney Disease (CKD)

| Stage | Description At risk | GFR (mL/min/1.73 m$^2$) 90-120 (with CKD symptoms) |
|---|---|---|
| 1 | Kidney damage with normal or elevated GFR | ≧90 |
| 2 | Kidney damage with mildly reduced GFR | 60-89 |
| 3 | Moderately reduced GFR | 30-59 |
| 4 | Severely reduced GFR | 15-29 |
| 5 | Kidney Failure (ESRD) | <15 (or dialysis) |

Hyperphosphatemia in CKD subjects has several secondary effects. When a subject suffers from hyperphosphatemia, excess serum phosphate precipitates serum calcium causing widespread ectopic extraskeletal calcification. Unwanted calcium deposits can occur in cardiovascular tissue, resulting in an increased risk of cardiovascular complications that often lead to death. Additionally, increased serum phosphate decreases intestinal calcium absorption. These two mechanisms work concurrently to reduce serum calcium levels.

A reduction in serum calcium levels can contribute to an increase in the production of parathyroid hormone (PTH) and to the development of secondary hyperparathyroidism. Furthermore, recent studies show that high phosphate levels can stimulate PTH production directly and lead to secondary hyperparathyroidism. Continual stimulation of PTH secretion induces hyperplasia of the parathyroid gland and may lead to a parathyroidectomy becoming necessary.

It is believed that the method of the present invention involving the administration of a lanthanum carbonate capsule formulation not only reduces plasma phosphate levels but ameliorates the effects of CKD in subjects susceptible to or having any of stages one to five CKD, including hyperphosphatemia, ectopic extraskeletal calcification, serum hypocalcemia, and secondary hyperparathyroidism. It should however, be understood that this invention is not limited to any particular biochemical or physiological mechanism.

A subject having a symptom or symptoms of chronic kidney disease (CKD) can be treated by administering to the subject a therapeutically effective amount of a lanthanum carbonate capsule formulation of the present application. As indicated above, the subject treated may be at risk for CKD or have any of stages one to five CKD as defined above. Subjects at risk for CKD or who have any of stages one to five CKD who may be treated may have one or more of the following symptoms: a blood phosphate level of above about 4.5 mg/dL, a plasma creatinine concentration of above about 1.6 mg/dL, a BUN of above about 20 mg/dL, any detectable amount of blood in the urine, a urine protein concentration above about 100 mg/dL, a urine albumin concentration above about 100 mg/dL, an intact parathyroid hormone concentration in the blood above about 150 pg/mL, an abnormal GFR, or combination thereof.

The present method may be utilized to prevent the progression of renal pathology, e.g., by treating a subject displaying one or more symptoms of stage one CKD to prevent the development of CKD in the subject or by treating a subject having stage one CKD to prevent progression of the disease to stage two CKD, and so on.

A subject having a symptom or symptoms of CKD can be treated for calcification of soft tissue associated with CKD by administering to the subject a therapeutically effective amount of a lanthanum carbonate capsule formulation of the present invention. Calcification can occur in any soft tissue. Soft tissue can include arterial tissue, cardiac muscle, heart valves, joints, skin and breast tissue.

A subject suffering from or having one or more symptoms of secondary hyperparathyroidism can be treated by administering to the subject a therapeutically effective amount of a lanthanum carbonate capsule formulation of the present application. Hyperparathyroidism is defined as a disease in a subject having an intact PTH level of about 150 pg/mL or greater. The symptoms of hyperparathyroidism include hypocalcaemia (i.e., a blood calcium level below about 8.5 mg/dL), hyperphosphatemia (i.e., a blood phosphate level of above about 4.5 mg/dL), and bone disorders (e.g., bone fractures or bone pain).

Administration of Pharmaceutical Capsules

The lanthanum carbonate capsule formulation can be orally administered to subjects in accordance with this invention in dosage forms varying from about 125 to about 2000 mg elemental lanthanum as lanthanum carbonate with or immediately after meals. A typical dosage for an adult can be, e.g., 375 mg-6000 mg elemental lanthanum as lanthanum carbonate daily. More preferably, the dosage is 375-3750 mg/day. The dose can be divided and taken with each meal, for example a 250, 350, or 500 mg capsule, e.g., three times per day. Serum phosphate levels can be monitored weekly and dosages can be modified until an optimal serum phosphate level is reached. Administration may be conducted in an uninterrupted regimen; such a regimen may be a long term regimen, e.g., a permanent regimen, for treating chronic conditions. Capsules can be chewed like a tablet or, for patients who have difficulty chewing, capsules can be opened and the contents can be sprinkled onto the tongue or onto food. Alternatively, capsules can be swallowed whole.

The lanthanum carbonate formulation is administered such that plasma levels of lanthanum are low, e.g., at least as low as those provided by a mean concentration curve where $C_{max}$, $T_{max}$, and AUC are preferably less than 1.5 ng/ml, about 12 hours, and less than 50 ng·hr/ml, respectively, for a dose of 3 g per day (e.g., 1 g three times per day). Preferably, the $C_{max}$ and AUC are less than 1.1 ng/ml and less than 32 ng·hr/ml, and desirably, $C_{max}$ and AUC are less than 0.5 ng/ml and less than 20 ng·hr/ml, for such dosage. $T_{max}$ values are essentially unaffected by dose and $C_{max}$ and AUC values vary linearly with dosage for oral dosages up to about 1500 mg/day. $C_{max}$ and AUC values plateau for dosages above about 1500 mg/day. All of these parameters have their common meanings.

It will be understood that the type of lanthanum carbonate formulation and the duration of the treatment will vary depending on the requirements for treatment of individual subjects. The precise dosage regimen will be determined by the attending physician or veterinarian who will, inter alia, consider factors such as body weight, age and specific symptoms. The physician or veterinarian may titrate the dosage of lanthanum carbonate administered to a subject to determine the correct dosage for treatment. For example, a physician can measure phosphate levels in a patient, prescribe a particular lanthanum carbonate dosage to the patient for a week, and evaluate after the week if the dosage is appropriate by remeasuring phosphate levels in the patient.

EXAMPLES

Compatibility Studies of 500 mg Lanthanum Carbonate Hydrate Immediate Release Capsules Lanthanum carbonate hydrate immediate release capsules were studied to determine their dissolution properties and to ensure that dissolution was unaffected after storage.

Examples 1-3 examine the cause of the decreased dissolution observed after storage of lanthanum carbonate capsules. Based on these experiments it was hypothesized that the gelatin of the capsule shell and the encapsulated magnesium stearate caused the decreased dissolution. Alternative lubricants to magnesium stearate were evaluated in place of magnesium stearate. Examples 4-9, 11, and 12 examine the dissolution properties of capsules containing alternative lubricants to replace magnesium stearate. Example 10 discloses the process for making the capsules tested in Examples 11 and 12.

Examples 1-9, 11, and 12 below each used the following dissolution method for determining the dissolution rate for lanthanum carbonate contained in 500 mg lanthanum carbonate hydrate immediate release capsules.

Preparation of Solutions

Preparation of Dissolution Medium (0.25 M HCl)

For the preparation of 10 liters of 0.25 M HCl, 232.5 mL of HCl 37% (available from Merck, Darmstadt, Germany) was transferred into a 10 i volumetric flask and filled to volume using deionized water. The volume was scaled depending on requirements.

Urotropin Solvent (1 mol/L) (Hexamine)

35.0 g urotropin (hexamethylenetetramine) (available from VWR, West Chester, Pa.) was dissolved in a 250 mL volumetric flask filled to volume with purified water.

Sodium Acetate Buffer pH 6.2 (0.2 mol/L)

16.4 g sodium acetate (available from Merck, Darmstadt, Germany) was dissolved in a 1000 mL volumetric flask filled to volume with purified water and adjusted to pH 6.2 with acetic acid (available from Merck, Darmstadt, Germany).

Xylenol Orange Indicator Solution 10 mg Xylenol orange tetra sodium salt (available from Merck, Darmstadt, Germany) was dissolved in 5 mL ethanol (available from Merck, Darmstadt, Germany) in a 10 mL volumetric flask and diluted to volume using purified water. The solution expired after 1 week.

Disodium EDTA (0.001 mol/L) Volumetric Standard Solution

The volumetric standard solution was prepared using a 1/10 volumetric dilution of commercially available standardized 0.01 mol/L EDTA (available from Fluka/Sigma Aldrich, St. Louis, Mo.).

Measuring Capsule Dissolution Over Time

A Sotax AT7 Smart (available from Sotax, Hopkinton, Mass.) with 6×900 mL dissolution vessels, 6 corresponding paddles (USP Type II at 50 rpm), and a Whatman GF/D (2.7 µm glass fiber) filter that complied with USP Apparatus 2 and JP Method 2 requirements were used to perform the dissolution. 900 mL of dissolution medium was allowed to equilibrate for at least 30 min in a dissolution bath at 37° C.±0.5° C. One capsule was then dropped into the dissolution medium. 15 mL of the medium was removed after 5, 10, 15, 30, and 45 minutes using an automatic fraction collector. 15 mL 0.025 M HCL replaced the removed medium at each time point.

To determine the amount of lanthanum ion in the sample, 40 mL of 0.2 mol/L sodium acetate solution pH 6.2 was added to 2.5 mL of removed medium. 0.25 mL of xylenol orange indicator solution was then added and the pH was adjusted to 5.5±0.1 using 1 mol/L hexamine or 0.25 mol/L HCL. The sample was then titrated using 0.001 mol/L disodium EDTA solution from a pink/lilac starting color to a straw color end point. The amount of EDTA solution was correlated to an amount of lanthanum ion in the medium. Lanthanum(III) oxide ($La_2O_3$) (Fluka 04052 available from Sigma Aldrich, St. Louis, Mo.) was used as a reference standard for the amount of lanthanum ion in solution in the titration analysis. Two or three capsules per formulation and condition were generally tested. It was clear from early studies that such small numbers of capsules could reliably show if dissolution rate was affected by the experimental variables under test.

Making the Capsule Formulations Tested in Examples 1-9

Prior to mixing, the ingredients were sieved with a 1.00 mm sieve. The lanthanum carbonate, dextrates (when present), and disintegrant (when present) were mixed for 10 minutes. The colloidal silicon dioxide (when present) was then added and mixed for 2 minutes. Lubricant (when present) was added and mixed for a further 2 minutes. After slugging to obtain a large tablet or roller compacting, the mixture was milled into a coarser powder with better flow properties than the original powders from which the slugs were made. (Unless otherwise stated, the mixture was slugged prior to milling.) The mixture was then sieved again with a 1.00 mm sieve.

Hard gelatin capsules were then filled with the lanthanum carbonate powders in an amount equal to 500 mg elemental lanthanum per capsules. Capsugel® (Peapack, N.J.) supplied Coni-Snap® hard gelatin capsules size 00 (0.95 mL volume; 0.917 inches closed length) having the below composition to encapsulate the lanthanum carbonate powders. The body of the capsule shell contained 2 wt % titanium dioxide, 13-16 wt % water, and 82-85 wt % gelatin. The cap of the capsule shell contained 0.1779 wt % indigotine (i.e., FD & C Blue 2), 0.171 wt % erythrosin (i.e., FD & C Red 3), 1.4779 wt % titanium dioxide, 13-16 wt % water, and the remainder being gelatin.

Example 1

Dissolution Profiles for Lanthanum Carbonate Capsules Stored at 60° C. for 2 Weeks Three batches of lanthanum carbonate capsules were manufactured: (1) 900911 made via roller compaction, (2) E341X010, a batch with the same formula as 900911 but made via slugging, and (3) E341X008, a batch made via slugging with crosscarmellose sodium as disintegrant in place of crospovidone.

The dissolution profiles for 3 capsules (E341X008, E341X010, and 910011, number of samples n=2) were determined before and after storage in a drying oven at 60° C. for 2 weeks as shown in FIG. 1. The formulation for each of the 3 capsules is shown in Table 2.

TABLE 2

Formulations tested for their dissolution profiles before and after storage at 60° C. for 2 weeks.

| Formulation E341X008 | | Formulation E341X010 | | Formulation 910011 | |
|---|---|---|---|---|---|
| Name | mg/dosi | Name | mg/dosi | Name | mg/dosi |
| Lanthanum carbonate | 954.0 | Lanthanum carbonate | 954.0 | Lanthanum carbonate | 954.0 |
| Dextrates | 87.7 | Dextrates | 87.7 | Dextrates | 87.7 |
| Colloidal silicon dioxide (Aerosil ® 200) | 11.0 | Colloidal silicon dioxide (Aerosil ® 200) | 11.0 | Colloidal silicon dioxide (Aerosil ® 200) | 11.0 |
| Croscarmellose Sodium | 44.0 | Crospovidone | 44.0 | Crospovidone | 44.0 |
| Magnesium stearate | 3.3 | Magnesium stearate | 3.3 | Magnesium stearate | 3.3 |

As shown in FIG. 1, the dissolution profiles for all capsules after storage at 60° C. for 2 weeks showed a delayed release with a 10 minutes lag time and a lanthanum carbonate dissolution of 35-55% after 45 minutes. Unstressed samples demonstrated a greater than 90% lanthanum carbonate dissolution after 30 minutes.

Capsules from batch number 900911 were also stored for one month at 25° C./60% RH, 30° C./60% RH and 45° C./75% RH. The dissolution rates of the stored capsules at all storage conditions decreased compared to prior to storage. The capsules after storage were less than 80% dissolved after 30 minutes.

Example 2

Dissolution Profiles for Compacted (i.e., Slugged) and Encapsulated Lanthanum Carbonate

TABLE 3

Formulation for testing preparation methods
Formulation E341X018

| Name | mg/dosi |
|---|---|
| Lanthanum carbonate | 954.0 |
| Dextrates | 87.7 |
| Colloidal silicon dioxide (Aerosil ® 200) | 11.0 |
| Crospovidone | 44.0 |
| Magnesium stearate | 3.3 |

Figure 2:
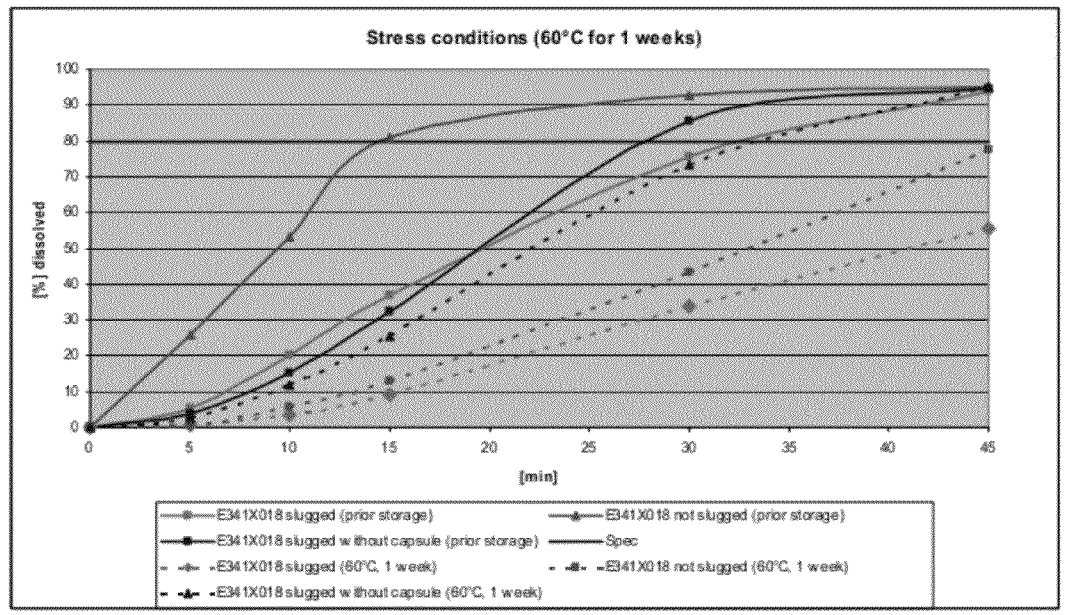
FIG. 2 is a graph comparing the dissolution rates before and after storage at 60° C. for 1 week of (1) a formulation that was slugged and encapsulated before storage, (2) a formulation that was not slugged, but encapsulated before storage, and (3) a formulation that was slugged before storage and encapsulated after storage.

To determine whether slugging or encapsulation affected dissolution rates, three different preparations based on formulation batch E341X018 (Table 3) were produced: (1) a formulation that was slugged and encapsulated prior to storage, (2) a formulation that was not slugged, but encapsulated prior to storage, and (3) a formulation that was slugged prior to storage and encapsulated after storage. The three preparations before and after storage in a drying oven at 60° C. for 1 week were tested for their dissolution properties (number of samples n=3). The dissolution profiles for the preparations before and after storage are displayed in FIG. 2.

Although storage delayed dissolution of each of the preparations compared to before storage, the slugged, unencapsulated prior to storage preparation was less affected by storage than the slugged, encapsulated preparation and the unslugged, encapsulated preparation. These results suggest that the gelatin capsule shell may contribute to the decreased dissolution rate.

Example 3

Impact of a Single Ingredient on the Dissolution Profile of Lanthanum Carbonate Capsules To determine whether a single ingredient in the capsule formulation affected dissolution rates, the dissolution profiles of formulations missing a single ingredient before and after storage in a drying oven at 60° C. for 1 week were determined. The base formulation, prior to removal of ingredients, is shown in Table 4.

TABLE 4

Base formulation prior to removal of ingredients
Basis Formulation

| Name | mg/dosi |
|---|---|
| Lanthanum carbonate | 954.0 |
| Dextrates | 87.7 |
| Colloidal silicon dioxide (Aerosil ® 200) | 11.0 |
| Crospovidone | 44.0 |
| Magnesium stearate | 3.3 |

Figure 3:
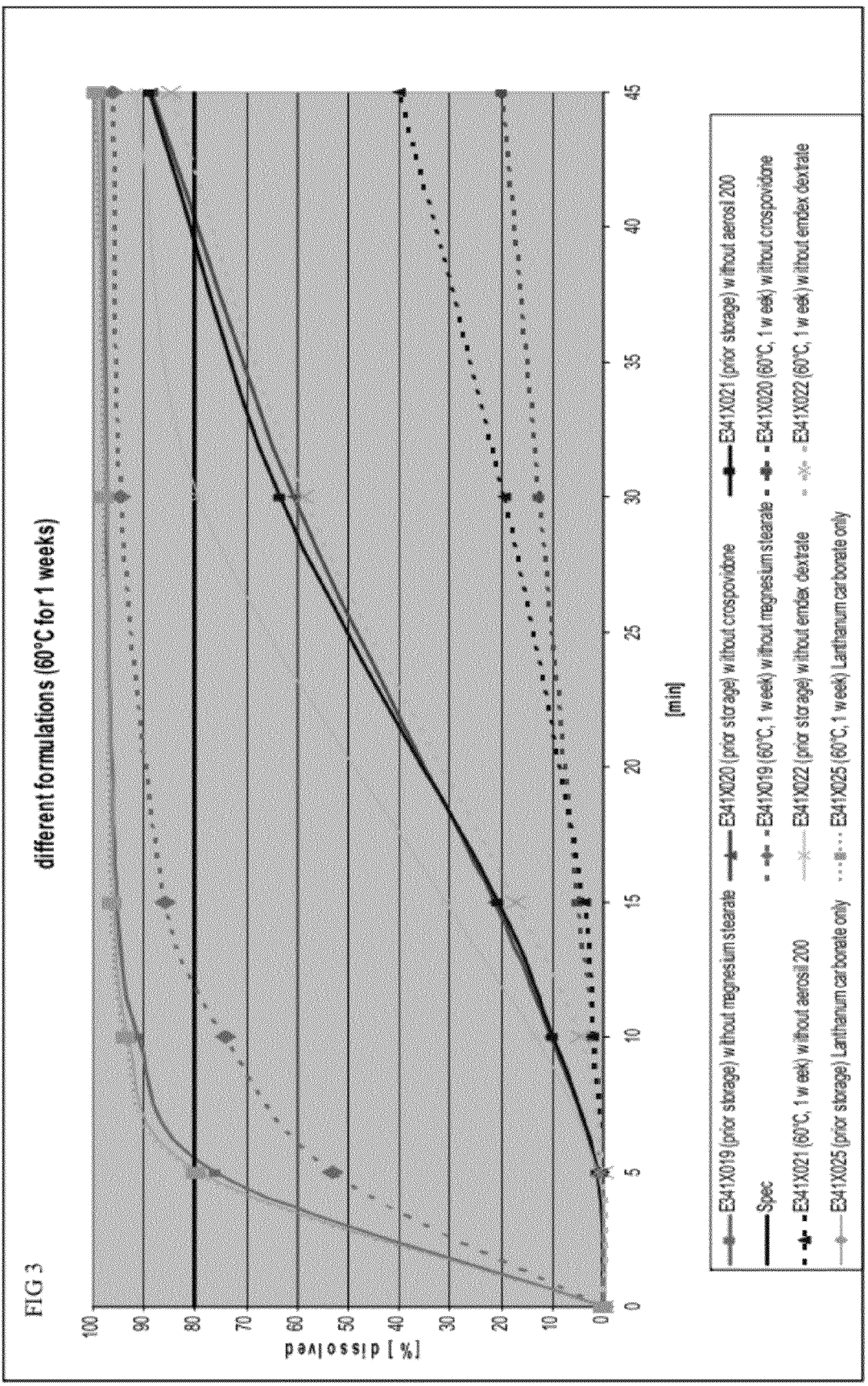
FIG. 3 is a graph comparing the dissolution profiles before and after storage at 60° C. for 1 week for the following formulations: (1) a formulation without magnesium stearate, (2) a formulation without colloidal silicon dioxide, (3) a formulation containing only lanthanum carbonate, (4) a formulation without crospovidone, and (5) a formulation without dextrates.

FIG. 3 provides the dissolution profiles before and after storage for the following formulations: (1) a formulation without magnesium stearate, (2) a formulation without colloidal silicon dioxide, (3) a formulation containing only lanthanum carbonate, (4) a formulation without crospovidone, and (5) a formulation without dextrates.

Formulations without magnesium stearate both prior to and after storage showed relatively fast dissolutions. The dissolution curves for formulations containing only lanthanum carbonate before and after storage were overlapping. Formulations without dextrates showed a delayed release profile with a lag of 5 minutes both before and after storage. Formulations without colloidal silicon dioxide and formulations without crospovidone both demonstrated a delayed release dissolution profile with a lag of 5 minutes prior to storage and a delayed release dissolution profile with a lag of 10 minutes after storage. All the formulations containing magnesium stearate had reduced dissolution rates after storage and it was deduced that the presence of magnesium stearate and the gelatin capsule shell were together responsible for the reduction in dissolution rate during storage.

Example 4

Dissolution Profiles for Lanthanum Carbonate Capsules Containing Magnesium Stearate, Glycerol Behenate, or Sodium Stearyl Fumarate Alternative lubricants were tested to determine their effect on the dissolution of lanthanum carbonate capsules before and after storage. As shown in Table 5, 4 formulations were tested: (1) a formulation containing magnesium stearate, (2) a formulation without a lubricant, (3) a formulation containing glycerol behenate instead of magnesium stearate, and (4) a formulation containing sodium stearyl fumarate instead of magnesium stearate.

TABLE 5

Formulations tested for their dissolution profiles before and after storage in a drying oven at 60° C. for 1 week.

| Name | mg/dosi | Name | mg/dosi |
|---|---|---|---|
| Formulation E341X018 | | Formulation E341X019 | |
| Lanthanum carbonate | 954.0 | Lanthanum carbonate | 1908.0 |
| Dextrates | 87.7 | Dextrates | 87.7 |
| Colloidal silicon dioxide (Aerosil ® 200) | 11.0 | Colloidal silicon dioxide (Aerosil ® 200) | 11.0 |
| Crospovidone | 44.0 | Crospovidone | 44.0 |
| Magnesium stearate | 3.3 | Magnesium stearate | 0.0 |
| Formulation E341X023 | | Formulation E341X024 | |
| Lanthanum carbonate | 954.0 | Lanthanum carbonate | 954.0 |
| Dextrates | 76.7 | Dextrates | 76.7 |
| Colloidal silicon dioxide (Aerosil ® 200) | 11.0 | Colloidal silicon dioxide (Aerosil ® 200) | 11.0 |
| Crospovidone | 44.0 | Crospovidone | 44.0 |
| Glycerol behenate | 11.0 | Sodium stearyl fumarate | 11.0 |

Figure 4:
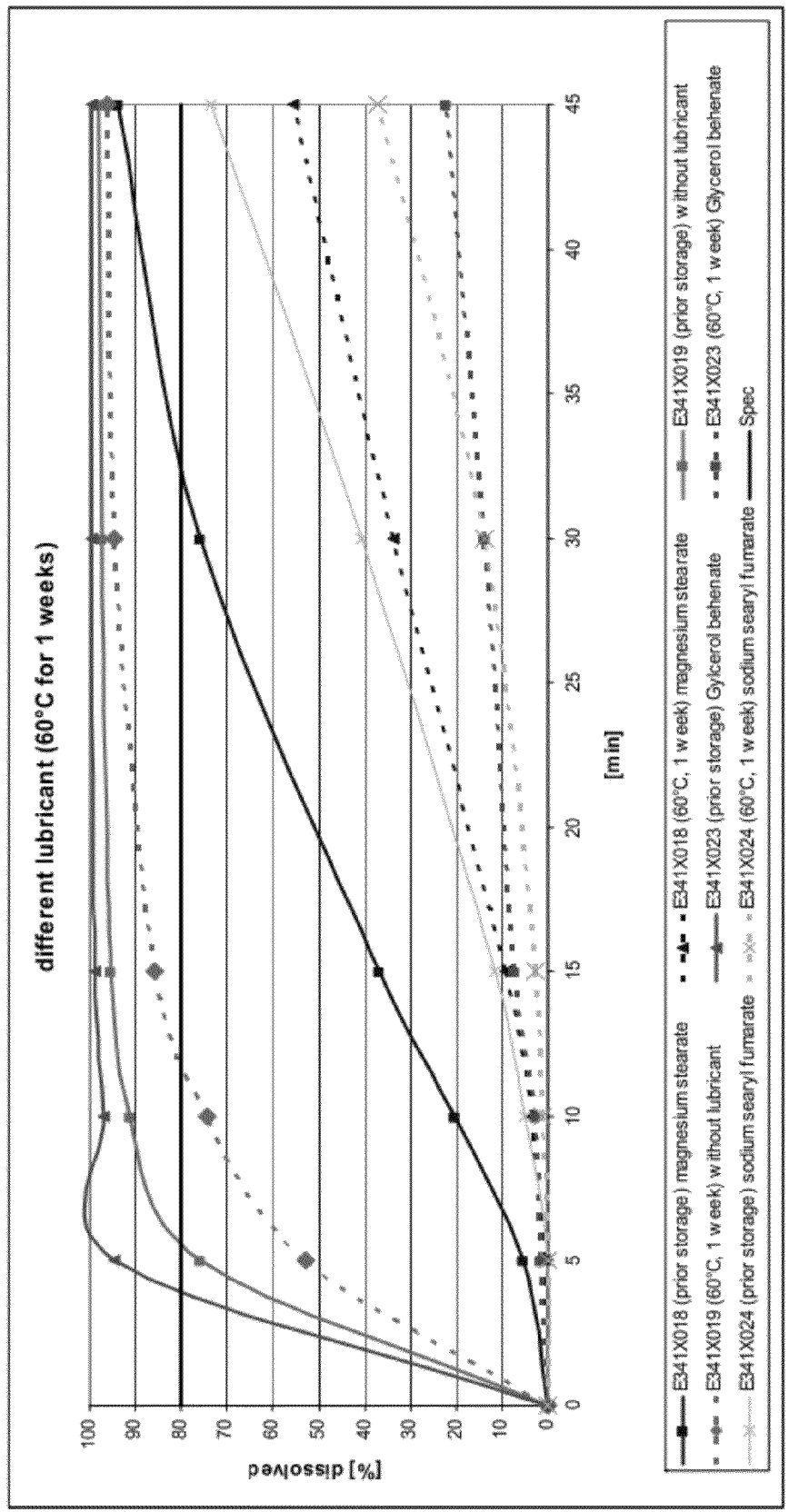
FIG. 4 is a graph comparing the dissolution profiles before and after storage at 60° C. for 1 week for the following formulations: (1) a formulation containing magnesium stearate, (2) a formulation without a lubricant, (3) a formulation containing glycerol behenate instead of magnesium stearate, and (4) a formulation containing sodium stearyl fumarate instead of magnesium stearate.

FIG. 4 discloses the dissolution curves for formulations containing different lubricants before and after storage in a drying oven at 60° C. for 1 week. Formulations containing magnesium stearate and formulations containing glycerol behenate had relatively fast dissolution profiles prior to storage and delayed release dissolution profiles with a lag of 5 minutes after storage. Formulations without a lubricant dissolved relatively fast both before and after storage. Formulations containing sodium stearyl fumarate had a delayed release dissolution profile with a lag of 5 minutes before storage and a delayed release dissolution profile with a lag of 10 minutes after storage.

Example 5

Dissolution Profiles for Lanthanum Carbonate Capsules Containing PEG 6000, L-Leucine, L-Leucine/PEG 6000, or Talc Alternative lubricants were tested to determine their effect on the dissolution of lanthanum carbonate capsules before and after storage in a drying oven at 60° C. for 1 week. As shown in Table 6, 4 formulations were tested each with a different lubricant: polyethyleneglycol, L-leucine, L-leucine/PEG 6000, or talc. The L-leucine/PEG 6000 lubricant is a mixture of 60 wt % L-leucine (available from Sigma-Aldrich, St. Louis, Mo.) and 40 wt % PEG 6000 (available from Croda, East Yorkshire, UK).

TABLE 6

Formulations tested for their dissolution profiles before and after storage at 60° C. for 1 week.
Formulations

| Name | mg/dosi |
|---|---|
| Lanthanum carbonate | 954.0 |
| Dextrates | 0.0 |
| Colloidal silicon dioxide (Aerosil ® 200) | 0.0 |
| Crospovidone | 0.0 |
| PEG 6000, L-leucine, L-leucine/PEG 6000, or talc | 55.0 |

Figure 5:
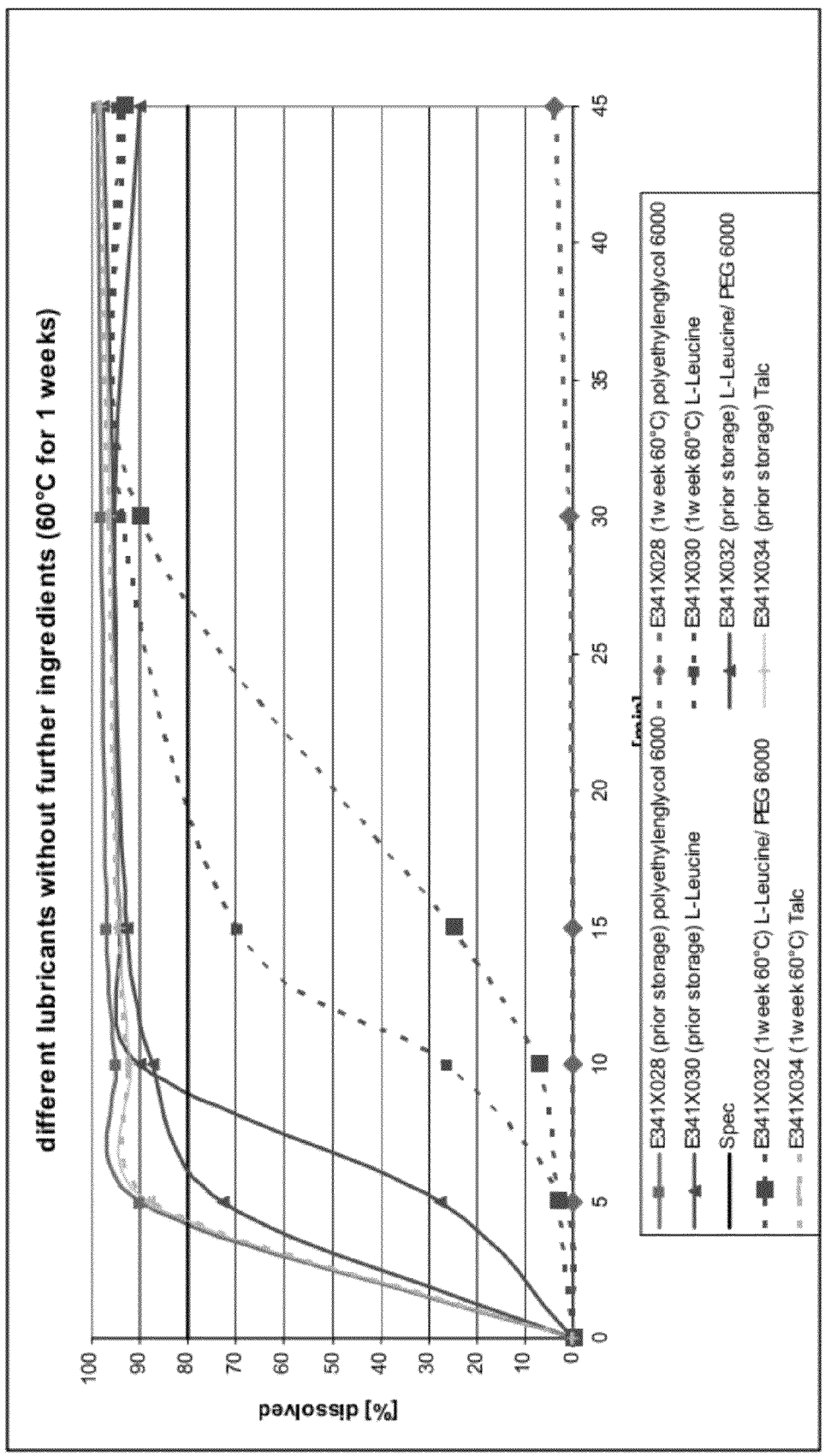
FIG. 5 is a graph comparing the dissolution profiles before and after storage at 60° C. for 1 week for the following formulations: (1) a formulation containing PEG 6000, (2) a formulation containing L-leucine, (3) a formulation containing L-leucine/PEG 6000, and (4) a formulation containing talc.

FIG. 5 discloses the dissolution curves for formulations containing different lubricants before and after storage in a drying oven at 60° C. for 1 week. Formulations containing PEG 6000 had a relatively fast dissolution profile prior to storage and showed no significant release after storage. Formulations containing L-leucine and formulations containing a mixture of L-leucine and PEG 6000 had a relatively fast dissolution profile prior to storage and showed a delayed release with a lag of 5 minutes after storage. Formulations containing talc had relatively fast dissolution profiles both before and after storage.

Example 6

Dissolution Profiles for Lanthanum Carbonate Capsules Containing LUBRITAB® or CUTINA® HR Alternative lubricants were tested to determine their affect on the dissolution of lanthanum carbonate capsules before and after storage in a drying oven at 60° C. for 1 week. As shown in Table 7, 2 formulations were tested each with a different lubricant: LUBRITAB® (hydrogenated vegetable oil and hydrogenated oil; available from J. Rettenmaier & Söhne GMBH+CO.KG, Rosenberg, Germany) or CUTINA® HR (hydrogenated castor oil; available from Cognis, Cincinnati, Ohio).

TABLE 7

Formulations tested for their dissolution profiles before and after storage at 60° C. for 1 week.
Formulations

| Name | mg/dosi |
|---|---|
| Lanthanum carbonate | 954.0 |
| Dextrates | 0.0 |
| Colloidal silicon dioxide (Aerosil ® 200) | 0.0 |
| Crospovidone | 0.0 |
| LUBRITAB ® or CUTINA ® HR | 55.0 |

Figure 6:
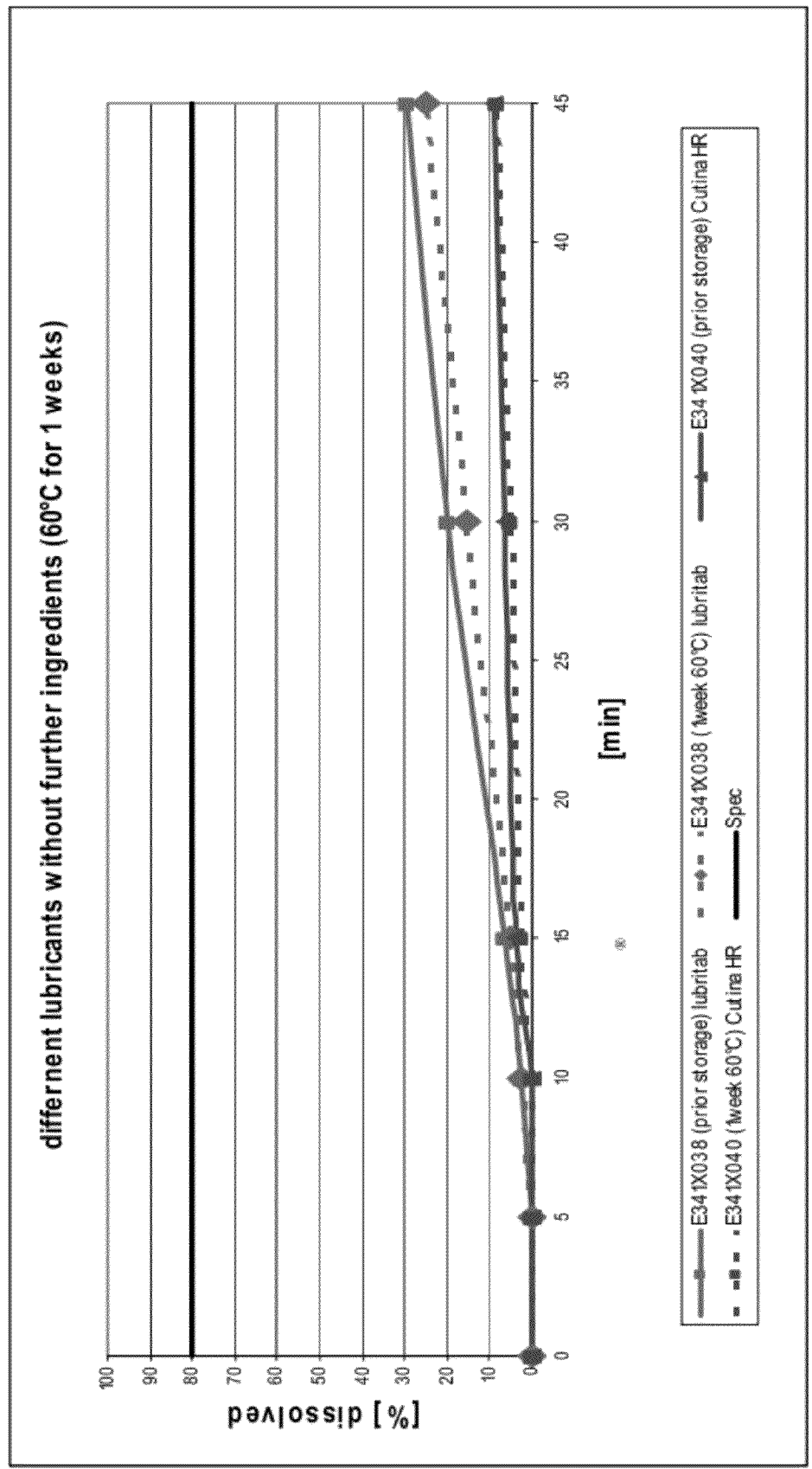
FIG. 6 is a graph comparing the dissolution profiles before and after storage at 60° C. for 1 week for the following formulations: (1) a formulation containing LUBRITAB® and (2) a formulation containing CUTINA® HR.

FIG. 6 discloses the dissolution curves for formulations containing different lubricants before and after storage at 60° C. for 1 week. Formulations containing LUBRITAB® had a delayed release profile with a lag of 5 minutes before and after storage although storage caused a more delayed release over time. Formulations containing CUTINA® HR tested before and after storage had similar delayed release profiles with a lag of 10 minutes.

Example 7

Dissolution Profiles for Lanthanum Carbonate Capsules Containing Either Dextrates, Colloidal Silicon Dioxide, Crospovidone, and L-Leucine or Only L-Leucine Lanthanum carbonate capsules containing either dextrates, colloidal silicon dioxide, crospovidone, and L-leucine or only L-leucine were tested to determine their affect on the dissolution of lanthanum carbonate capsules before and after storage in a drying oven at 60° C. for 1 week. As shown in Table 8, 2 formulations were tested.

TABLE 8

Formulations tested for their dissolution profiles before and after storage at 60° C. for 1 week.

| Formulation E341X030 | | Formulation E341X031 | |
|---|---|---|---|
| Name | mg/dosi | Name | mg/dosi |
| Lanthanum carbonate | 954.0 | Lanthanum carbonate | 954.0 |
| Dextrates | 0.0 | Dextrates | 36.0 |
| Colloidal silicon dioxide (Aerosil ® 200) | 0.0 | Colloidal silicon dioxide (Aerosil ® 200) | 11.0 |
| Crospovidone | 0.0 | Crospovidone | 44.0 |
| L-Leucine | 55.0 | L-Leucine | 55.0 |

Figure 7:
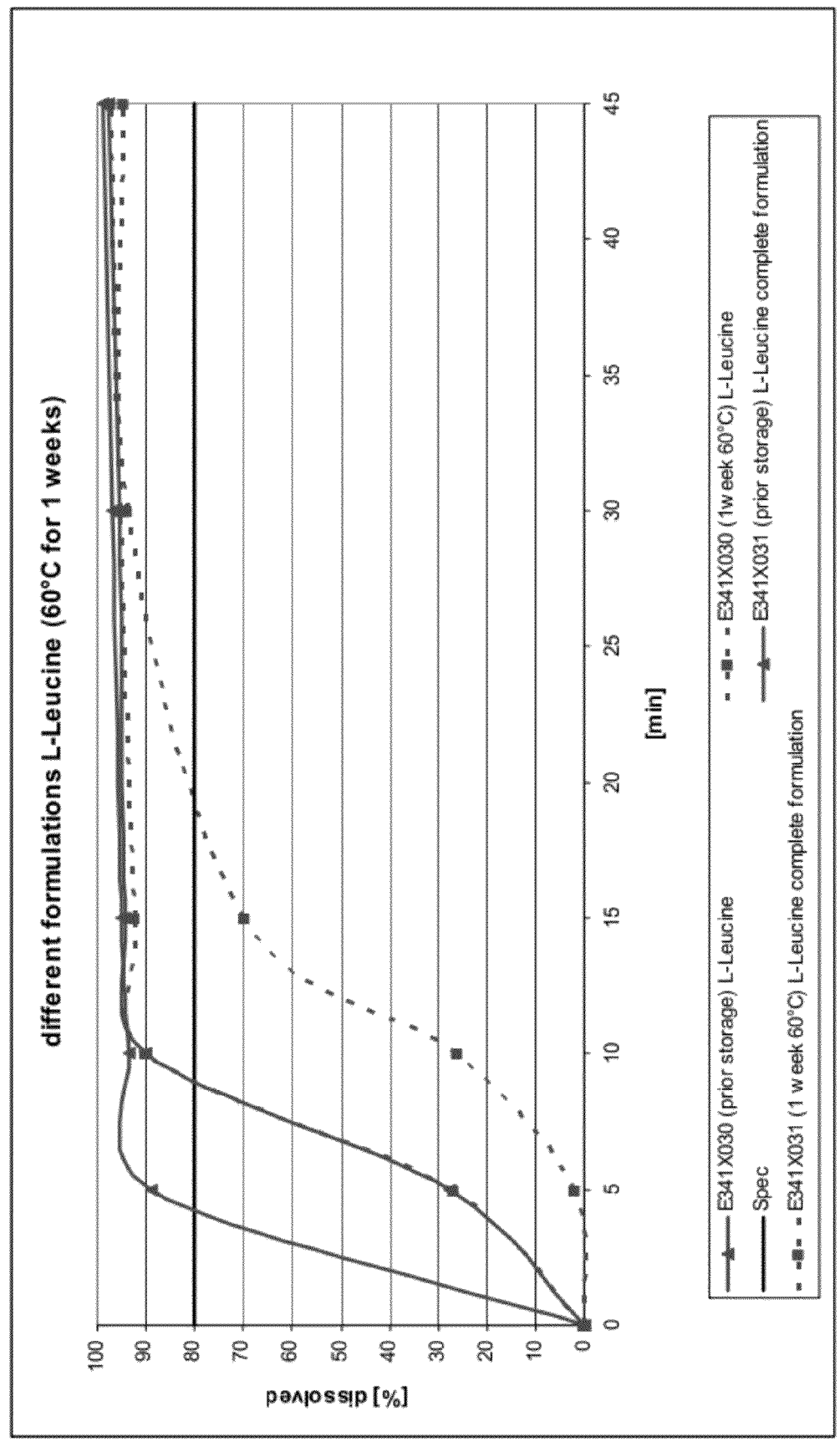
FIG. 7 is a graph comparing the dissolution profiles before and after storage at 60° C. for 1 week for the following formulations: (1) a lanthanum carbonate formulation containing only L-leucine and (2) a lanthanum carbonate formulation containing dextrates, colloidal silicon dioxide, crospovidone, and L-leucine.

FIG. 7 discloses the dissolution curves for the 2 formulations before and after storage at 60° C. for 1 week. Lanthanum carbonate formulations containing only L-leucine had a relatively fast release profile before storage and had a delayed release profile with a lag of 5 minutes after storage. Lanthanum carbonate formulations containing dextrates, colloidal silicon dioxide, crospovidone, and L-leucine after storage released at a slower rate compared to before storage.

Example 8

Dissolution Profiles for Lanthanum Carbonate Capsules Containing PEG 6000 Before and after Storage at 60° C. for 1 Week or 50° C. for 1 Week Lanthanum carbonate capsules containing PEG 6000 were tested to determine their dissolution before and after storage at 60° C. for 1 week or 50° C. for 1 week. As shown in Table 9, the following formulation was tested.

TABLE 9

Formulation tested for its dissolution profiles before and after storage at 60° C. for 1 week or 50° C. for 1 week.
Formulations

| Name | mg/dosi |
|---|---|
| Lanthanum carbonate | 954.0 |
| Dextrates | 0.0 |
| Colloidal silicon dioxide (Aerosil ® 200) | 0.0 |
| Crospovidone | 0.0 |
| PEG 6000 | 55.0 |

Figure 8:
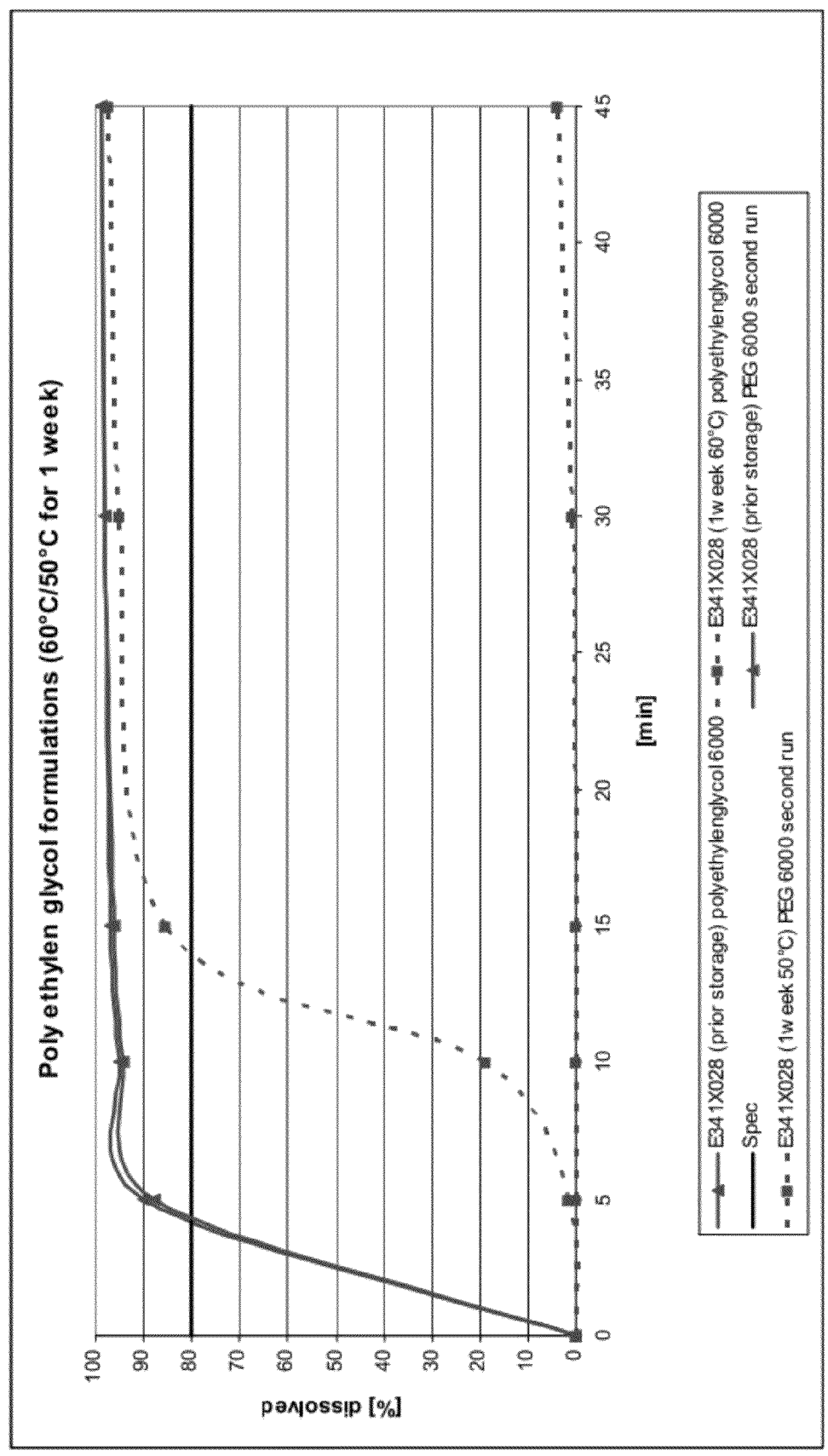
FIG. 8 is a graph comparing the dissolution profiles for lanthanum carbonate capsules containing PEG 6000 before and after storage at 60° C. for 1 week or 50° C. for 1 week.

FIG. 8 discloses the dissolution curves for the formulation before and after storage at 60° C. for 1 week or 50° C. for 1 week. Testing at 50° C. was performed since the melting point of PEG 6000 is 55° C. Formulations prior to storage showed a relatively fast dissolution profile. Formulations after storage at 50° C. for 1 week showed a delayed release with a lag of 5 minutes while formulations after storage at 60° C. for 1 week showed no significant release.

Example 9

Dissolution Profiles for Lanthanum Carbonate Capsules Containing Either Dextrates, Colloidal Silicon Dioxide, Crospovidone, and Talc or Only Talc Lanthanum carbonate capsules containing dextrates, colloidal silicon dioxide, crospovidone, and talc were tested to determine their dissolution before and after storage in a drying oven at 60° C. for 1 or 2 weeks. Lanthanum carbonate capsules containing only talc were tested to determine their dissolution before and after storage at 60° C. for 1 week. As shown in Table 10, the following formulations were tested.

TABLE 10

Formulations tested for their dissolution profiles before and after storage at 60° C. for 1 or 2 weeks.

| Formulation E341X034 | | Formulation E341X035 | |
|---|---|---|---|
| Name | mg/dosi | Name | mg/dosi |
| Lanthanum carbonate | 954.0 | Lanthanum carbonate | 954.0 |
| Dextrates | 0.0 | Dextrates | 36.0 |
| Colloidal silicon dioxide (Aerosil ® 200) | 0.0 | Colloidal silicon dioxide (Aerosil ® 200) | 11.0 |
| Crospovidone | 0.0 | Crospovidone | 44.0 |
| Talc | 55.0 | Talc | 55.0 |

Figure 9:
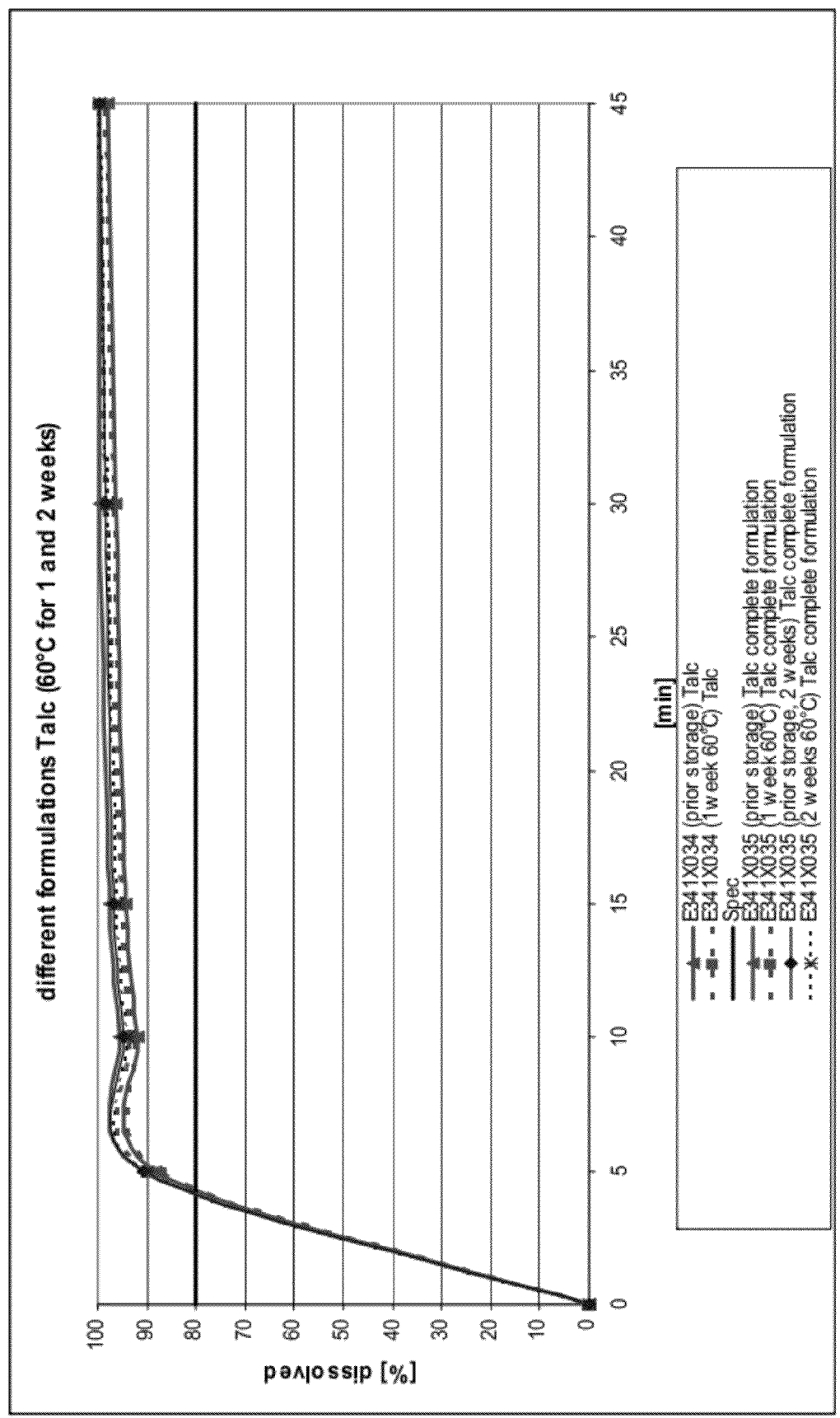
FIG. 9 is a graph comparing the dissolution profiles for lanthanum carbonate capsules containing dextrates, colloidal silicon dioxide, crospovidone, and talc before and after storage at 60° C. for 1 or 2 weeks and for lanthanum carbonate capsules containing only talc before and after storage at 60° C. for 1 week.

FIG. 9 discloses the dissolution curves for the formulations before and after storage at 60° C. for 1 or 2 weeks. All formulations prior to and after storage provided relatively fast dissolution profiles. Talc is a temperature stable lubricant for lanthanum carbonate capsules.

Example 10

Manufacturing of Lanthanum Carbonate Capsules Containing Talc

TABLE 11

Ingredients for the Lanthanum Carbonate Capsule

| Ingredient | batch | amount | % (wt/wt) |
|---|---|---|---|
| Lanthanum carbonate | 1845634 | 954.0 mg | 86.7 |
| Dextrates (Emdex ®) | 474620 | 90.7 mg | 8.2 |
| Colloidal silicon dioxide (Aerosil ® 200) | 1926183 | 11.0 mg | 1.0 |
| Crospovidone | 2200764 | 44.0 mg | 4.0 |
| Talc | 1910860 | 0.275 mg | 0.025 |

The ingredients in Table 11 were weighed to a batch size of 104.5 kg and sieved with a 1 mm hand sieve. Lanthanum carbonate, dextrates and crospovidone were then blended for 10 min on a tumble blender. The colloidal silicon dioxide was then added and blended for a further 2 minutes at 6 rpm and finally the talc was added and blended for a further 2 minutes at 6 rpm.

The blend was then compacted on a compactor (Bepex Pharmapaktor L 200/50 P, Hosokawa Micron Ltd., UK). The compaction was performed in 2 sub-batches of about 41 Kg for sub-batch 1 (batch no.: E341X043) and about 56 kg for sub-batch 2 (batch no.: E341X044) using two different settings for the roller compression force to optimize the process parameter. Both compaction settings produced properly compacted material. Table 12 lists the different settings.

TABLE 12

Compactor Settings

| | Setting 1 | Setting 2 |
|---|---|---|
| Screw size | 3 | 3 |
| Screw rotation (rpm) | 48 | 77 |
| Roller compression force (kN) | 29 | 35 |
| Roller type (corrugated) | 4.1 | 4.1 |
| Roller rotation (rpm) | 7.7 | 12.2 |
| Sieve size (mm) | 1.25 | 1.25 |
| Sieve rotation (rpm) | 56 | 77 |

Physical characteristics of the blend as shown in Table 13 were determined.

TABLE 13

Physical Characteristics of Final Blend

| | Method | Results Setting 1 (E341X043) | | Results Setting 2 (E341X044) | |
|---|---|---|---|---|---|
| Bulk density | Ph. Eur. 2.9.15 | 1.000 | | 0.980 | |
| Tapped density | Ph. Eur. 2.9.15 | 1.282 | | 1.250 | |
| Hausner-ratio | — | 1.282 | | 1.275 | |
| Particle Size distribution | Ph. Eur. 2.9.16 | <63 μm | 23.3% | <63 μm | 15.4% |
| | | 63-90 μm | 11.9% | 63-90 μm | 10.6% |
| | | 90-125 μm | 9.8% | 90-125 μm | 13.8% |
| | | 125-250 μm | 18.0% | 125-250 μm | 18.9% |
| | | 250-500 μm | 21.6% | 250-500 μm | 23.0% |
| | | 500-710 μm | 11.7% | 500-710 μm | 12.3% |
| | | 710-1000 μm | 3.7% | 710-1000 μm | 5.9% |
| | | 1000-1250 μm | 0.2% | 1000-1250 μm | 0.1% |
| | | >1250 μm | 0.0% | >1250 μm | 0.0% |

The material processed on setting 2 showed a lower amount of fine particles which could be an advantage for the filing of capsules. There are no significant differences between Bulk and tapped density.

Both final blends in an amount equal to 500 mg elemental lanthanum were filled into Coni-Snap® hard gelatine capsules size 00 (available from Capsugel®, Peapack, N.J.) using a capsule filler (GKF 1500 or KKE 1500 available from Bosch, Brooklyn Park, Minn.). For the purpose of evaluation of process robustness, two different speeds for the filler were used (90 cycles/min and 100 cycles/min). The machine runs steadily with both speeds but capsule filling runs more smoothly with compaction setting 2 in comparison with compaction setting 1.

Example 11

Dissolution Testing of Lanthanum Carbonate Capsules Containing Talc

Figure 10:
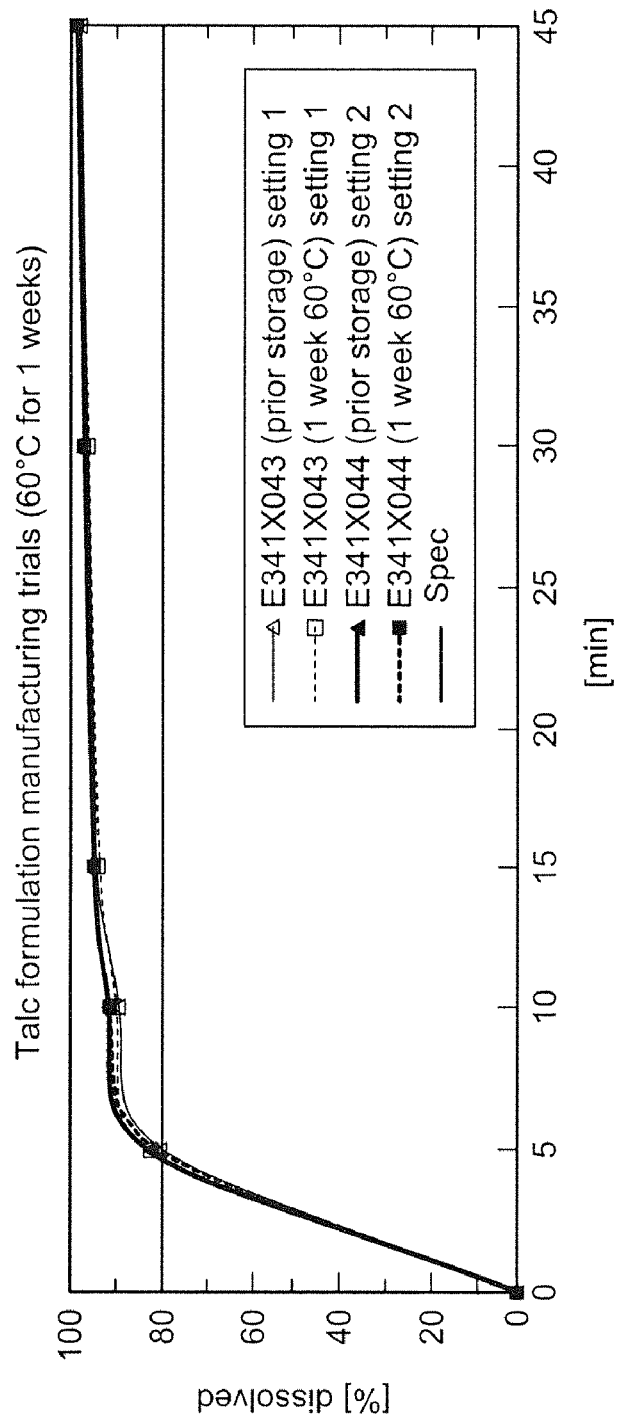
FIG. 10 is a graph comparing the dissolution profiles for lanthanum carbonate capsules containing dextrates, colloidal silicon dioxide, crospovidone, and talc before and after storage at 60° C. for 1 week.

The capsules (E341X043 and E341X044) were stored at room temperature and in stressed conditions in a drying oven at 60° C. for one week and were tested for their dissolution properties. The results are presented in Table 14 and FIG. 10.

TABLE 14

Tablet dissolution results for tablets stored at room temperature and at 60° C. for 1 week

| Dissolution time point [min] | Batch E341X043 | | Batch E341X044 | |
|---|---|---|---|---|
| | Room temperature | One week at 60° C. | Room temperature | One week at 60° C. |
| 5 | 79.8 | 82.2 | 83.3 | 80.7 |
| 10 | 89.2 | 89.6 | 91.6 | 91.4 |
| 15 | 94.6 | 93.7 | 95.3 | 95.2 |
| 30 | 96.8 | 96.0 | 97.6 | 97.4 |
| 45 | 98.6 | 98.4 | 99.2 | 98.8 |

All dissolution profiles fulfilled the specification of greater than 80% lanthanum carbonate dissolution after 30 minutes. A decreasing of the dissolution rate after storage for one week at 60° C. in comparison with room temperature was not evident. The results showed no significant difference between the two batches. The results showed that the talc can be used as lubricant for manufacturing of lanthanum carbonate capsules with no significant effect on the dissolution rate compared to the storage condition.

Example 12

Long Term Stability Testing of Lanthanum Carbonate 500 mg Capsules

Capsules were manufactured according to Example 10 and placed on a long term stability test. Table 15 provides stability data after 4 weeks.

TABLE 15

Stability Data for Lanthanum Carbonate 500 mg Capsules; Lot 1005001; 200 mL HDPE Bottle with Polypropylene Closure, 90 Count

| Storage Time | Appearance | Lanthanum Assay (%) | Moisture (% w/w) | Lanthanum Hydroxycarbonate | | Dissolution (%) |
|---|---|---|---|---|---|---|
| | | | | Polymorph I | Polymorph II | |
| Specification | Hard gelatin capsule with opaque purple cap printed S405, opaque white body printed 500 mg and containing a white to off-white granulate. | 90-110% | Record | Not more than 1.8% | Not more than 2.0% | Q = 80% after 30 minutes |
| Initial 25° C./60% RH | Complies | 98.2 | 1.6 | Complies | Complies | 97 |
| 4 weeks 30° C./75% RH | Complies | 99.5 | 1.7 | Complies | Complies | 97 |
| 4 weeks 40° C./75% RH | Complies | 99.4 | 1.6 | Complies | Complies | 97 |
| 4 weeks | Complies | 98.6 | 1.2 | Complies | Complies | 95 |

Data showed no change or essentially no change in the percent dissolution after 30 minutes in 0.25 M HCl after storage at 25° C./60% RH, 30° C./75% RH, or 40° C./75% RH for 4 weeks. Capsules from this batch are used in a clinical study to evaluate the bioavailability of lanthanum carbonate from capsules relative to that from tablets.

The present invention is not to be limited in scope by the specific embodiments described herein. Indeed, various modifications of the invention in addition to those described herein will be apparent to those skilled in the art from the foregoing description. Such modifications are intended to fall within the scope of the appended claims.

All references cited herein, including all patents, published patent applications, and published scientific articles and books, are incorporated by reference in their entireties for all purposes.

The invention claimed is:

1. An oral pharmaceutical capsule comprising a shell, lanthanum carbonate or lanthanum carbonate hydrate, and talc in an amount from about 0.01% to about 0.05% by weight of the capsule contents, wherein the shell encapsulates the lanthanum carbonate or lanthanum hydrate and the talc.

2. The capsule of claim 1, wherein the shell comprises gelatin.

3. The capsule of claim 2, wherein the gelatin is in an amount from about 10% to about 95% by weight of the shell.

4. The capsule of claim 1, wherein after the capsule is stored at 50° C. or 60° C. for 1 or 2 weeks, the lanthanum carbonate or lanthanum carbonate hydrate of the capsule is at least 80% dissolved after 30 minutes in 0.25 M HCl.

5. The capsule of claim 1, wherein the lanthanum carbonate or lanthanum carbonate hydrate has the formula:

$$La_2(CO_3)_3 \cdot nH_2O$$

wherein n has a value from 0 to 10.

6. The capsule of claim 5, wherein n has a value from 3 to 6.

7. The capsule of claim 1, wherein the lanthanum carbonate or lanthanum carbonate hydrate is in an amount from about 50% to about 95% by weight of the capsule contents.

8. The capsule of claim 1, further comprising a diluent encapsulated in the shell.

9. The capsule of claim 8, wherein the diluent is dextrates.

10. The capsule of claim 8, wherein the diluent is in an amount from about 5% to about 50% by weight of the capsule contents.

11. The capsule of claim 1, further comprising a flow aid encapsulated in the shell.

12. The capsule of claim 11, wherein the flow aid is colloidal silicon dioxide.

13. The capsule of claim 1, wherein the flow aid is in an amount from about 0.1% to about 4.0% by weight of the capsule contents.

14. The capsule of claim 1, further comprising a disintegrant encapsulated in the shell.

15. The capsule of claim 14, wherein the disintegrant is in an amount from about 1.0% to about 15% by weight of the capsule contents.

16. The capsule of claim 1 comprising (1) 86.7 wt % lanthanum carbonate hydrate, (2) 8.2 wt % dextrates, (3) 1.0 wt % colloidal silicon dioxide, (4) 4.0 wt % crospovidone, and (5) 0.025 wt % talc, wherein the shell encapsulates the lanthanum carbonate hydrate, dextrates, colloidal silicon dioxide, crospovidone, and talc and the weight percentages are based on the weight of the capsule contents.

* * * * *

UNITED STATES PATENT AND TRADEMARK OFFICE
CERTIFICATE OF CORRECTION

| | | |
|---|---|---|
| PATENT NO. | : 8,263,119 B2 | |
| APPLICATION NO. | : 12/958380 | |
| DATED | : September 11, 2012 | |
| INVENTOR(S) | : Roger Withington | |

It is certified that error appears in the above-identified patent and that said Letters Patent is hereby corrected as shown below:

In the Specifications:

In column 6, line 14, delete "alph-" and insert -- alpha- --, therefor.

In column 6, line 50, delete "Toronoto," and insert -- Toronto, --, therefor.

In column 7, line 41, delete "rocalcitrol)." and insert -- rocaltrol). --, therefor.

In column 11, line 48, delete "10 i" and insert -- 10 L --, therefor.

In column 13, line 2, delete "crosscarmellose" and insert -- croscarmellose --, therefor.

In the Claims:

In column 22, line 17, in Claim 13, delete "claim 1," and insert -- claim 11, --, therefor.

Signed and Sealed this
Fourth Day of December, 2012

David J. Kappos
*Director of the United States Patent and Trademark Office*